United States Patent [19]

Floyd, Jr. et al.

[11] Patent Number: 5,440,647
[45] Date of Patent: Aug. 8, 1995

[54] X-RAY PROCEDURE FOR REMOVING SCATTERED RADIATION AND ENHANCING SIGNAL-TO-NOISE RATIO (SNR)

[75] Inventors: Carey E. Floyd, Jr., Chapel Hill; Alan H. Baydush, Durham, both of N.C.

[73] Assignee: Duke University, Durham, N.C.

[21] Appl. No.: 52,185

[22] Filed: Apr. 22, 1993

[51] Int. Cl.⁶ ............................................. G06K 9/00
[52] U.S. Cl. ................................ 382/132; 264/413.19; 382/275
[58] Field of Search .................... 382/6, 54, 56.52, 30, 382/49; 250/330; 364/413.14, 413.19, 413.22, 413.17, 413.18

[56] References Cited

U.S. PATENT DOCUMENTS

| | | | |
|---|---|---|---|
| 1,164,987 | 12/1915 | Bucky | 364/713 |
| 4,590,582 | 5/1986 | Umemura | 364/724 |
| 4,599,742 | 7/1986 | Kikuchi et al. | 378/99 |
| 4,734,770 | 3/1988 | Matsuba | 358/167 |
| 4,845,762 | 7/1989 | Higashi | 378/99 |
| 4,866,785 | 9/1989 | Shibano | 382/49 |
| 4,868,857 | 9/1989 | Dobbins, III | 378/99 |
| 4,916,722 | 4/1990 | Ema | 378/99 |
| 4,916,745 | 4/1990 | Hart et al. | 382/6 |
| 4,918,713 | 4/1990 | Honda | 378/99 |
| 4,920,491 | 4/1990 | Eberhard et al. | 364/413.19 |
| 4,920,501 | 4/1990 | Sullivan et al. | 364/518 |
| 4,951,305 | 8/1990 | Moore et al. | 378/147 |
| 4,969,110 | 11/1990 | Little et al. | 364/550 |
| 5,140,538 | 8/1992 | Bass et al. | 364/602 |
| 5,168,161 | 12/1992 | Markandey | 250/330 |

OTHER PUBLICATIONS

Albert Rose, "The Sensitivity Performance of the Human Eye on an Absolute Scale", *Journal of the Optical Society of America* (Feb., 1948), vol. 38, No. 2, pp. 196–208.

Geman et al., "Stochastic Relaxation, Gibbs Distributions, and the Bayesian Restoration of Images", IEEE Transactions on Pattern *Analysis and Machine Intelligence* (Nov., 1984), vol. PAMI-6, No. 6, pp. 721–741.

Vardi et al., "A Statistical Model for Positron Emission Tomography", Journal of the American Statistical Association (Mar., 1985), vol. 80, No. 389, pp. 8–25.

Geman et al., "Statistical Methods for Tomographic Image Reconstruction", *Bulletin of the ISI* (1987), vol 52, pp. 1–18.

Love et al., "Scatter Estimation for a Digital Radiographic System Using Convolution Filtering", *Medical Physics*, vol. 14, No. 2, pp. 178–185. (Mar./Apr. 87).

Seibert et al., "X-Ray Scatter Removal by Deconvolution", *Medical Physics*, vol. 15, No. 4, pp. 567–575 (Jul.-/Aug. 1988).

Floyd et al., "Scatter Compensation in Digital Chest Radiography Using Fourier Deconvolution", *Investigative Radiology*, vol. 24, No. 1, pp. 30–33 (Jan. 1989).

Hebert et al., "A Generalized EM Algorithm for 3-D Bayesian Reconstruction from Poisson Data Using Gibbs Priors", *IEEE Transactions on Medical Imaging*, vol. 8, No. 2, pp. 194–202 (Jun. 1989).

Liang et al., "On Bayesian Image Reconstruction from Projections: Uniform and Nonuniform A Priori Source Information", *IEEE Transactions on Medical Imaging*, vol. 8, No. 3, pp. 227–235 (Sep. 1989).

Green, "Bayesian Reconstructions from Emission Tomography Data Using a Modified EM Algorithm", *IEEE Transactions on Medical Imaging*, vol. 9, No. 1, pp. 84–93 (Mar. 1990).

Chan et al., "Studies of Performance of Antiscatter Grids in Digital Radiography: Effect on Signal-to-Noise Ratio", *Medical Physics*, vol. 17, No. 4, pp. 655–664 (Jul./.Aug. 1990).

(List continued on next page.)

*Primary Examiner*—Joseph Mancuso
*Attorney, Agent, or Firm*—Richard E. Jenkins

[57] ABSTRACT

An improved projection radiography procedure which provides for simultaneously removing scattered radiation and reducing noise with a Bayesian statistical estimation algorithm that results in an enhanced signal-to-noise ratio (SNR).

11 Claims, 5 Drawing Sheets

OTHER PUBLICATIONS

Chotas et al., "Single-Exposure Conventional and Computed Radiography Image Acquisition", *Investigative Radiology*, vol. 26, No. 5, pp. 438–445 (1991).

Floyd et al., "Posterior Beam-Stop Method for Scatter Fraction Measurement in Digital Radiography", vol. 27, No. 2, pp. 119–123, *Investigative Radiology* (1991).

Neitzel, "Grids or Air Gaps for Scatter Reduction in Digital Radiography: A Model Calculation", *Medical Physics*, vol. 19, No. 2, pp. 475–481 (Mar./Apr. 1992).

Lalush et al., "Simulation Evaluation of Gibbs Prior Distributions for use in Maximum A Posteriori SPECT Reconstructions", *IEEE Transactions in Medical Imaging*, vol. 11, No. 2, pp. 267–275 (Jun. 1992).

Floyd et al., "Scatter Compensation for Digital Chest Radiography Using Maximum Likelihood Expectation Maximization", *Investigative Radiology*, vol. 28, No. 5, pp. 427–433 (1933).

X-RAY PROCEDURE FOR REMOVING SCATTERED RADIATION AND ENHANCING SIGNAL-TO-NOISE RATIO (SNR)

TECHNICAL FIELD

This invention relates to a method for improving x-ray diagnostic imaging, and more particularly to an improved projection radiography procedure which provides for both removing scattered radiation and improving the signal-to-noise ratio (SNR).

RELATED ART

The unwanted detection of scattered photons in chest radiography and the like has long been recognized as a source of background which decreases image contrast and increases noise. Scattered x-rays can account for 95% of the detected x-ray flux in the mediastinum region and up to 70% in the lung in patient radiographs. These "scatter" photons are deflected from their original line of flight and the misinformation which they contribute to the image appears qualitatively as loss of image contrast and increased noise.

Efforts to compensate for scattered photons fall in two categories: (1) physical removal before detection; and (2) numerical compensation applied to the image after acquisition.

Several techniques have been implemented to numerically compensate chest images for the average effects of scatter. These algorithms all increase contrast by removing a smooth estimate of the scattered component. Unfortunately, these techniques do not remove the variance due to the scatter and so they result in a net decrease in SNR. While the technique of unsharp masking effectively subtracts a low spatial frequency component from the image to increase contrast but has not been shown to significantly improve SNR.

For all of the above reasons, an object of the present invention is to provide a novel method whereby projection radiography imaging is enhanced by utilizing a numerical technique which both removes scattered radiation and enhances the signal-to-noise ratio (SNR) of the image.

SUMMARY OF THE INVENTION

In accordance with the present invention, applicants provide a method for increasing the signal-to-noise ratio (SNR) in projection radiography imaging comprising subjecting an object under examination to projection radiography so as to obtain measured imaging parameter data; transforming said measured imaging parameter data to digital imaging data; altering said digital imaging data to compensate for scattered radiation from said projection radiography; simultaneously altering said digital imaging data to reduce the noise therein from said projection radiography; and forming an enhanced image of the object under examination having an increased signal-to-noise ratio (SNR).

DETAILED DESCRIPTION OF THE PREFERRED EMBODIMENT OF THE INVENTION

Applicants have developed a Bayesian statistical estimation technique for improving the ratio of signal-to-noise (SNR) in digital chest radiographs and the like. This algorithm employs Bayes' rule to estimate a scatter-reduced image and incorporates prior information about the statistical properties of radiographic image noise.

As is well known, the visual quality of a chest radiograph or the like is degraded by the detection of scattered x-rays as well as by Poisson noise. The Bayesian estimation algorithm simultaneously compensates for both of these effects. Contrast is restored by correcting for an estimate of the scattered x-rays in the detected image. Noise is decreased by including prior information about expected image smoothness into the estimation algorithm. These compensations result in a higher signal-to-noise ratio (SNR). While window and level adjustment in digital radiography provide arbitrary contrast enhancement, window and level adjustment do not improve SNR.

The presence of scattered photons in a radiographic image decreases contrast by adding a non-uniform background. While a level adjustment in a digital display will remove a constant background, the background due to scatter is non-uniform and cannot be removed by level adjustment. Two approaches have been investigated to reduce the impact of scattered x-rays on radiographic images. The first is to reduce the number of scattered photons which are acquired and the second is to compensate the image for scattered protons after acquisition. To reduce the number of scattered x-rays which reach the detector, grids and air gaps are typically used. With conventional screen-film radiography, the patient dose must be increased (a factor of three to eight) to ensure that the total detected flux is restored for proper film exposure. Digital radiography, however, allows more latitude for correct exposure.

Recent studies have evaluated the performance of grids and air gaps for digital radiography (see Neitzel, U., "Grids or Air Gaps for Scatter Reduction in Digital Radiography: A Model Calculation" *Medical Physics,* 1992, 19:475–482; and Chan, et al., "Studies of Performance of Antiscatter Grids in Digital Radiography: Effect on Signal-to-Noise Ratio" *Medical Physics,* 1990, 17:655–664). Since both grids and air gaps reduce the detected scatter at the cost of losing some non-scattered flux, applicants desired to investigate numerical post-processing algorithms to reduce the effects of scattered radiation without the loss of primary photons. As an alternative to grids and air gaps, several of these numerical techniques have been proposed to reduce the effect of scattered x-rays on the acquired image. These numerical post-processing techniques typically consist of a linear (convolution) technique for estimating the scatter content from the acquired image and then subtracting this estimated scatter from the original measured image. Unfortunately, such estimation-subtraction techniques in the past acted to decrease SNR.

Applicants applied statistical estimation algorithms to digital chest radiography. In the first implementation, applicants developed a Maximum Likelihood Expectation Maximization (MLEM) technique to estimate a scatter-reduced image (see Floyd, et al., "Scatter Compensation for Digital Chest Radiography Using Maximum Likelihood Expectation Maximization", *Investigative Radiology*, May, 1993). This MLEM algorithm dramatically increased contrast, but also significantly increased noise for a net increased SNR in the lung and a slight decrease in the mediastinum region. The increase in noise when using MLEM is well known in applications to reconstruction of emission computed tomographic (ECT) images. An effective solution to this noise problem has been achieved for ECT through Bayesian estimation techniques (see Hebert, T. and Leahy, R., "A Generalized EM Algorithm for 3-D Bayesian Reconstruction from Poisson Data Using Gibbs Priors" *IEEE Transactions on Medical Imaging*, 1989, 8:194–202; Liang, et al., "On Bayesian Image Reconstruction from Projections: Uniform and Nonuniform A Priori Source Information", *IEEE Transactions on Medical Imaging*, 1989, 8:227–235; Green, P., "Bayesian Reconstructions from Emission Tomography Data Using a Modified EM Algorithm" *IEEE Transactions on Medical Imaging*, 1990, 9:84–93; and Lalush, D. S. and Tusi, B. M., "Simulation Evaluation of Gibbs Prior Distributions for Use in Maximum A Posteriori SPECT Reconstructions" IEEE Transactions On Medical Imaging, 1992, 11:267–275).

However, applicants have discovered a Bayesian restoration algorithm for digital chest radiography and the like with projection radiography which increases contrast with little or no increase in noise for a net increase in SNR and thus an implied increase in detectability for low contrast features. This successful application of the algorithm to projection radiography is unexpected and surprising to one of ordinary skill in the art.

Contrast improvement is achieved by reducing the contribution of scattered photons to the image. This scatter reduction is performed simultaneously with noise constraint using a Bayesian Maximum a posteriori (MAP) estimation technique (see Geman, S. and Geman, D., "Stochastic Relaxation, Gibbs Distributions, and the Bayesian Restoration of Images" *IEEE Transactions on Pattern Analysis and Machine Intelligence*, 1984, PAMI-6:721–741) which was previously developed for image reconstruction in emission computed tomography (ECT) (see Hebert, T. and Leahy, R., "A Generalized EM Algorithm for 3-D Bayesian Reconstruction from Poisson Data Using Gibbs Priors" *IEEE Transactions on Medical Imaging*, 1989, 8:194–202; Liang, et al., "On Bayesian Image Reconstruction from Projections: Uniform and Nonuniform A Priori Source Information" *IEEE Transactions on Medical Imaging*, 1989, 8:227–235; Green, P., "Bayesian Reconstructions from Emission Tomography Data Using a Modified EM Algorithm" *IEEE Transactions on Medical Imaging*, 1990, 9:84–93; and Lalush, D. S. and Tusi, B. M., "Simulation Evaluation of Gibbs Prior Distributions for Use in Maximum A Posteriori SPECT Reconstructions" *IEEE Transactions on Medical Imaging*, 1992, 11:267–275).

This estimation technique differs from other scatter reduction techniques which subtract or deconvolve some approximation of the scatter photon contribution from the measured image. In the Bayesian approach, the compensated image is estimated from the measured image given prior information regarding the photon scatter and image noise. To clarify this description, consider that scatter and noise corrupt the ideal image. The Bayesian MAP algorithm provides an estimate of the ideal image when given the measured image and some a priori information about the measuring process.

Testing of Method of the Invention

Figure 1:
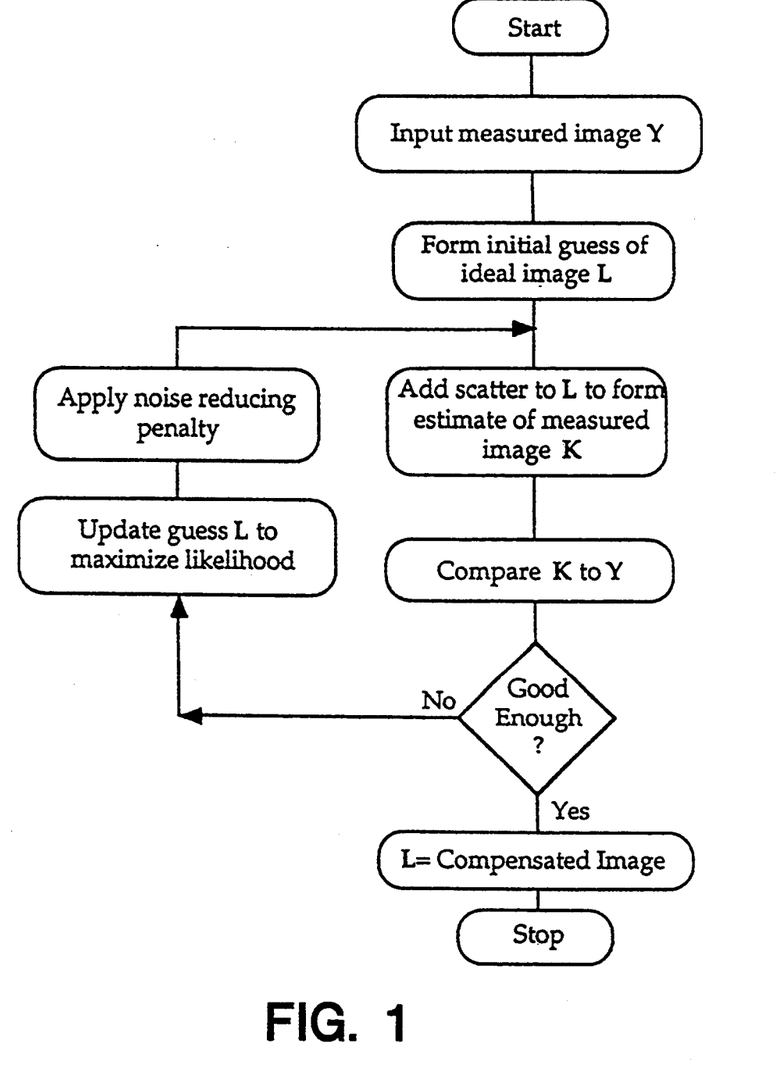
FIG. 1 is a flow chart of a Bayesian restoration algorithm used in the practice of the present invention.

The MAP algorithm (shown in FIG. 1) starts with a guess L for the ideal image, uses this guess to estimate a measured image K, compares this estimate K to the actual measured image Y, and then modifies the guess L to improve the agreement between the measured image Y and the estimated image K. For each pixel in the modified guess, the pixel's intensity is compared with the values in its neighborhood. If the difference is small, then there is a probability that the intensity variation is due to noise and this variation will be penalized through the algorithm. If the variation is large, then the variation is probably due to structure in the image and the variation is allowed. The modified guess is the starting point for a new iteration. At each iteration, the new guess is closer to the ideal image and the increase in noise is constrained. This cycle is repeated. In practice, the amount of change in the image is less at each iteration. Typically, iteration is stopped after 5 to 20 iterations.

The initial guess is arbitrary. Here applicants investigated two initializations: (1) the measured image (which has roughly the correct shape but having scatter and noise) and (2) a uniform image where each pixel is initialized to a constant value (which has no noise, but is far from the correct shape). Applicants also examined several smoothed versions of the image as starting points, but these did not yield improved results.

The prior information about scattered x-rays comes from several previous studies which evaluated different models of how to estimate the scatter content of an image (see Love, L. A. and Kruger, R. A., "Scatter Estimation for a Digital Radiographic System Using Convolution Filtering" *Medical Physics*, 1987, 14: 178–185; Seibert, J. A. and Boone,, J. M., "X-Ray Scatter Removal by Deconvolution", *Medical Physics*, 1988 15:567–575; and , Floyd, et al., "Scatter Compensation in Digital Chest Radiography by Fourier Deconvolution", *Investigative Radiology*, 1989, 24:30–33).

Image Acquisition

Exposure technique typical of portable bedside radiography was used. Exposures were made at 95 kV, 1.25 mAs using a GE AMX portable x-ray unit with a 36 by 43 cm field of view. Beam filtration was 3 mm Aluminum. Source-to-image distance was 102 cm. Images were acquired using a photostimulable phosphor x-ray imaging system (PPS) (Philips Computed Radiography model 901). The imaging plates were 367 cm×43 cm (14"×17") and were sampled at 1760 by 2140 square pixels (called 2 k images hereafter) at the PPS processor. Type III plates were used. All plates were processed by the plate reader using fixed speed and latitude to facilitate conversion of the digital image values to calibrated exposure values.

Digital images were transferred to an image processing computer network. Most images were then resampled to 1024×1024 pixel format (called 1 k images hereafter) by averaging adjacent pixels. The 1 k images were used to facilitate computation for the contrast, noise, and SNR experiments. The full resolution 2 k images were used for the resolution experiments and for radiologists' subjective interpretation. In addition, all images were converted to exposure values in floating point representation for computation. The full 10-bit intensity resolution was maintained throughout the acquisition, transfer, and resampling steps.

Evaluation

Improvements in nodule detectability are best measured using human performance receiver operating characteristic (ROC) studies. However, ROC studies require extensive human as well as processing resources to achieve statistically significant measurements. Since object detectability is related to SNR through the Rose model (see Rose, A., "The Sensitivity Performance of the Human Eye on an Absolute Scale" *Journal of the Optical Society of America*, 1948, 38:196–208), applicants developed and evaluated the algorithm used in the present invention by using more simple criteria: contrast, noise, and signal-to-noise ratio for a low contrast polystyrene disk superimposed on an anatomical phantom.

To measure changes in contrast, noise, and signal-to-noise ratio, applicants imaged an anatomical phantom (manufactured by Humanoid Systems of Carson, Calif.) both with and without a tissue-equivalent (12 mm thick polystyrene) disk superimposed at three anatomical locations: the upper lobe of the left lung, the retrocardiac region, and the mediastinum. In the lung, the disk provided a contrast of 0.10 in the measured images. The images were then restored separately using the Bayesian algorithm. The restored images with and without the contrast disk were registered and subtracted to yield a difference image. In practice, perfect registration was difficult to achieve due in part to variation in the registration of the phosphor imaging plates within the plate reader. This registration error results in slight shifting and rotation of the digital images. To avoid altering the noise in the images, interpolation was not used to achieve registration. Instead, six exposures were made for each of the images and from these six exposures applicants selected the pair which most nearly could be aligned by a whole pixel shift. Adequate registration was achieved by this procedure.

The digital pixel values in the images are proportional to the logarithm of the exposure. Average signal values were measured in 30×30 pixel (12×12 mm) regions: one located inside the boundary of the disk and one at the same location in the image without the disk. Contrast was defined as the difference between these two average values.

Noise was measured as the standard deviation from the mean in the same ROI in the background (without disk) image. The ratio of these contrast and noise measurements is the SNR. Since the noise in the images does not have a uniform frequency distribution, the size of the ROI used will affect the estimate of noise from the image. In the tests, the 30×30 pixel ROI was chosen to fit within the disk. The noise measurement within this ROI represents an integration of the two dimensional noise power spectrum from the Nyquist frequency of 16.7 cm$^{-1}$ down to 1.2 cm$^{-1}$. While estimation of the full noise power spectrum would be informative, the integration over this range is practical and provides sufficient information.

Resolution

The noise reduction operates to decrease the difference between a pixel and its neighbors. Here applicants defined a pixel neighborhood to include the pixel and those adjacent to it in the North, South, East, and West directions. The strength of this smoothing is a function of the intensity difference defined by the Gibbs prior distribution data described herein. Since any smoothing might result in a loss of image resolution, applicants examined the resolution degradation as a function of iteration. The MAP algorithm is non-linear and so a modulation transfer function (MTF) analysis is inappropriate; the algorithm's behavior will depend on the content of the image.

Accepting that the general effect of this Bayesian MAP estimator on resolution cannot be completely characterized, applicants performed an operational evaluation. The step response function (see Chotas, et al., "Single-Exposure Conventional and CR Image Acquisition" *Investigative Radiology*, 1991, 26:438–445) was examined for different step heights for pixel by pixel variations. Applicants embedded an alternating step pattern into the lung region of a chest phantom image as follows. A 20×70 pixel region was selected in the upper lung and was replaced by the mean value of the region. Alternating pixel rows were set to a test value in an interior 10×50 sub-region. In separate experiments, five test values were used representing exposure contrasts of 1, 2, 3, 4, and 5%. The images were reconstructed and the step heights were measured over the sub-region as a function of iteration. It should be appreciated that the neighborhood for the noise reduction is calculated by pixel distance and thus the results of this resolution test will be valid at any pixel resolution (1 k×1 k or 2 k ×2 k). Therefore, while this test was performed on 1 k by 1 k pixel images, conclusions from this test will scale up to 2 k by 2 k images.

Test Results

A. Contrast, Noise, and SNR

Figure 2A:
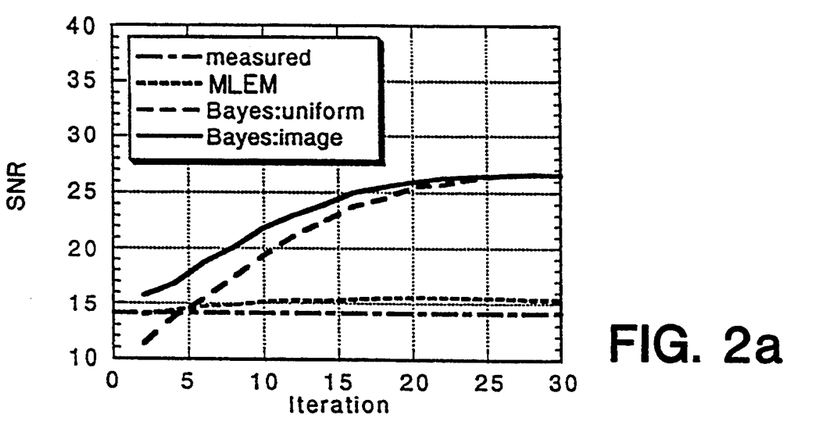
FIG. 2 is a graph illustrating imaging of a polystyrene disk in the lung utilizing (1) a solid curve representing the Bayesian algorithm with the image as an initial guess; (2) a dashed curve representing the Bayesian algorithm with a uniform initial guess; (3) a dotted curve representing the MLEM algorithm with the image as an initial guess; and (4) an alternating long and short dashed horizontal line representing the measured image.
Figure 2B:
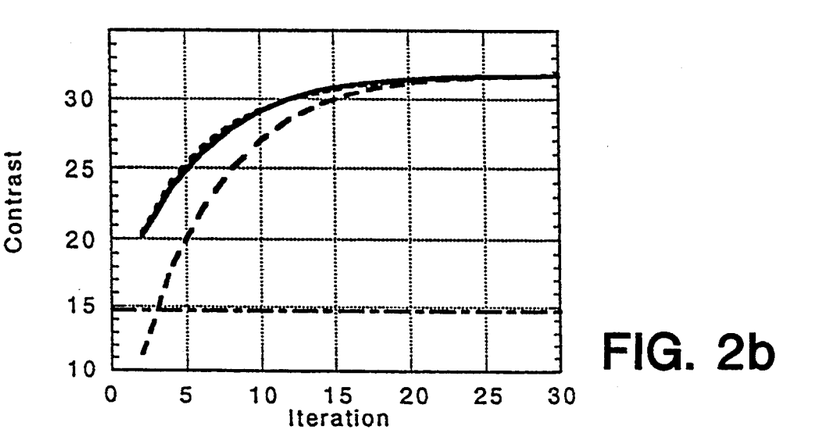
Figure 2C:
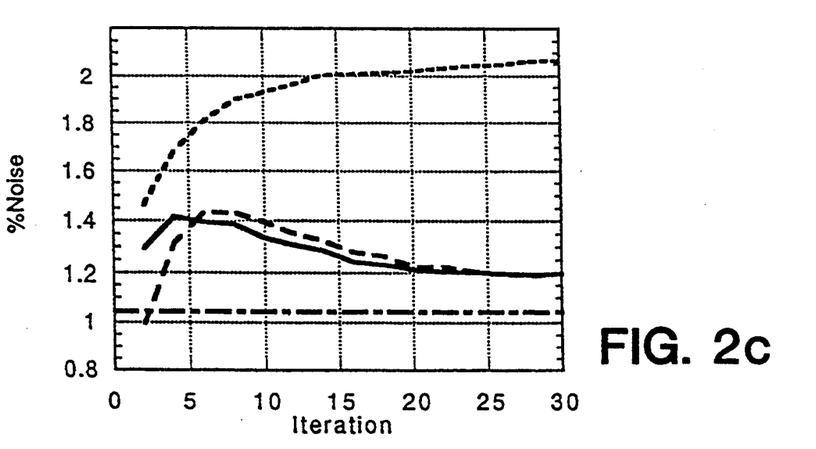

Contrast, noise, and SNR results are shown in FIG. 2 for evaluation of the polystyrene disk located in the lung region of the chest phantom. Four curves are shown for each plot: the solid curve represents the Bayesian algorithm with the image as an initial guess; the dashed curve represents the Bayesian algorithm with a uniform initial guess; the dotted curve represents the MLEM algorithm with the image as an initial guess; the alternating long and short dashed horizontal line represents the measured image.

As can be seen from FIG. 2a, the Bayesian algorithm approaches convergence at 30 iterations with an SNR which is a factor of 1.8 greater than in the initial image, regardless of initialization. The Bayesian result is significantly superior to the MLEM. Both the MLEM and the Bayesian algorithms converge to the same contrast (a factor of two greater than in the measured image). The source of the difference in SNR for the three algorithms is evident from examining the image noise plotted in FIG. 2b. The Bayesian algorithm initially increased the noise above that of the measured image, but decreased after early iterations and asymptotically approached a value that is only 20 percent above the measured image. The MLEM algorithm, on the other hand, starts with a value that is 50% higher than the measured image and increases with iteration, achieving a value over twice that of the measured image by iteration 30. It can be seen that the improved SNR, which is associated with the Bayesian algorithms, is due to significant contrast enhancement associated with containment of the noise.

Figure 3A:
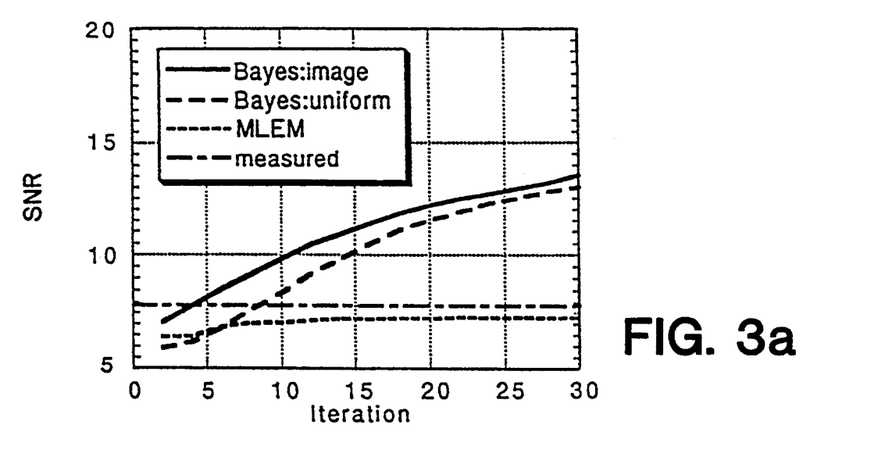
FIG. 3 is a graph similar to FIG. 2 except illustrating imaging results for a polystyrene disk in the retrocardiac region (versus the lung region of FIG. 2)
Figure 3B:
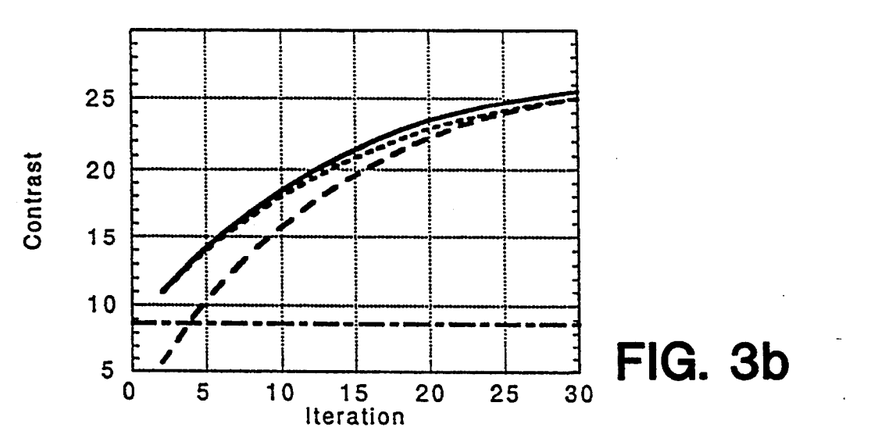
Figure 3C:
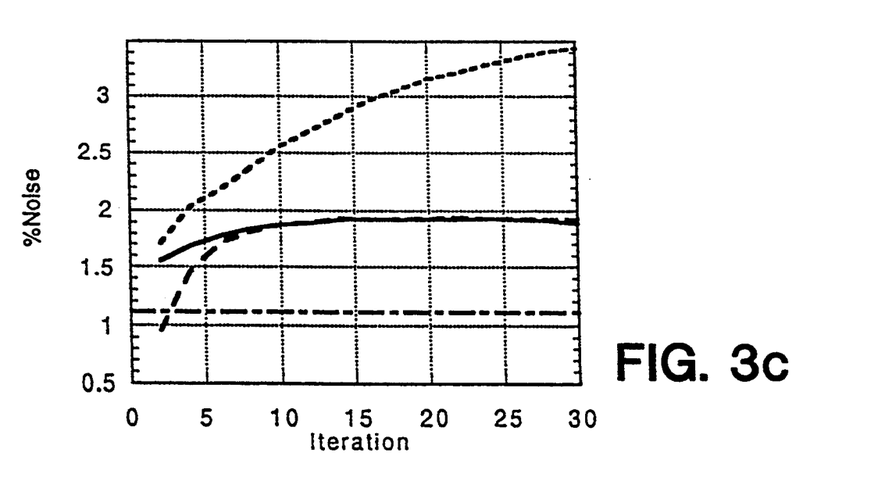

SNR results for the polystyrene disk in the retrocardiac region, shown in FIG. 3, demonstrate behavior which is similar to that shown in FIG. 2 for the lung region. The best results for SNR were obtained when the Bayesian algorithm was initialized with the image followed by the Bayesian algorithm initialized with the uniform image. In the retrocardiac region (not shown), the MLEM algorithm never achieved the SNR of the original image. While the noise for MLEM continued to increase with iteration up to a factor of 3.5 times that of the measured image at 30 iterations, the Bayesian algorithm converged to a stable noise value of about 1.2 times that of the measured image by 20 iterations. Thus, it can be inferred that the signal to noise for the Bayesian algorithms will continue to increase at higher iterations in this region as the contrast increases.

B. Resolution

The alternating pixel row test was performed for five test values representing pixel differences (percent contrast) of 1,2,3,4, and 5. No resolution degradation was expected for large pixel differences and indeed no degradation was observed for difference of 4,5, and 3%. Differences of 2% showed some evidence of smoothing, but only after 20 iterations. Differences of 1% were smoothed out after 4 iterations.

C. Phantom Images

Figure 4:
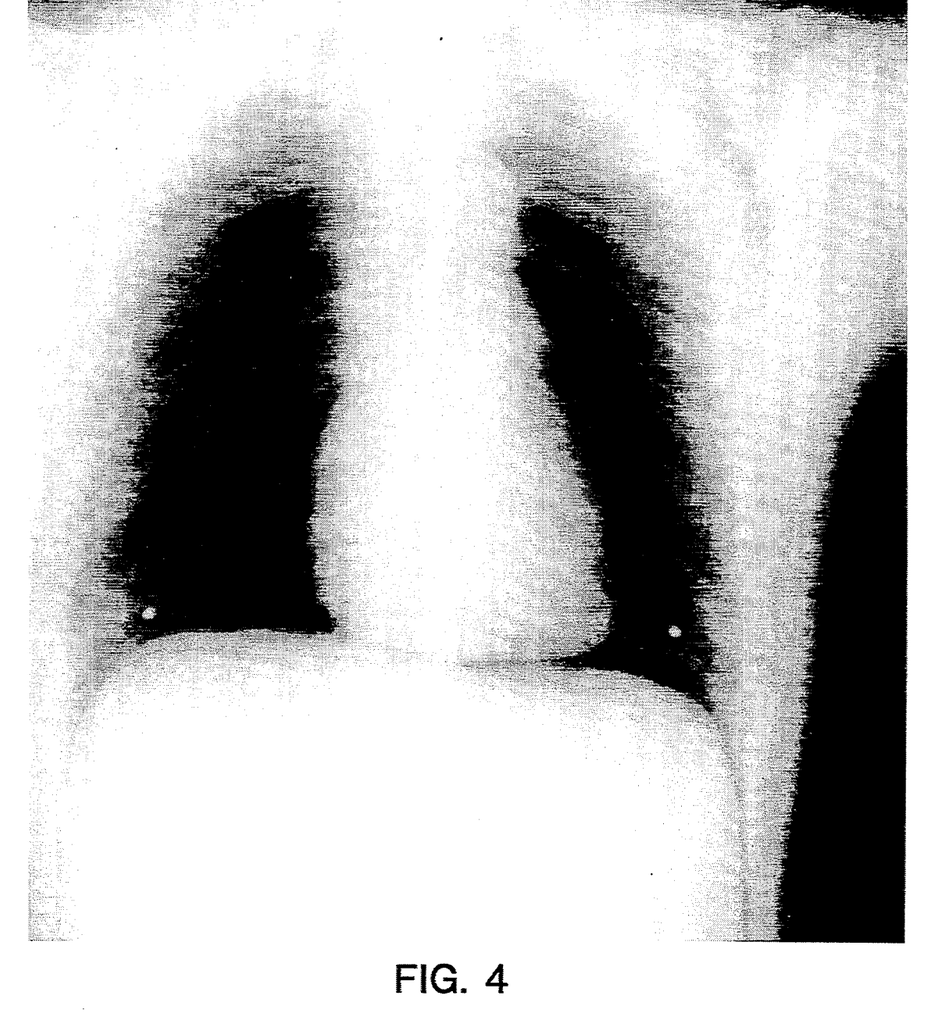
FIG. 4 is an image of an anthropomorphic chest phantom.
Figure 5:
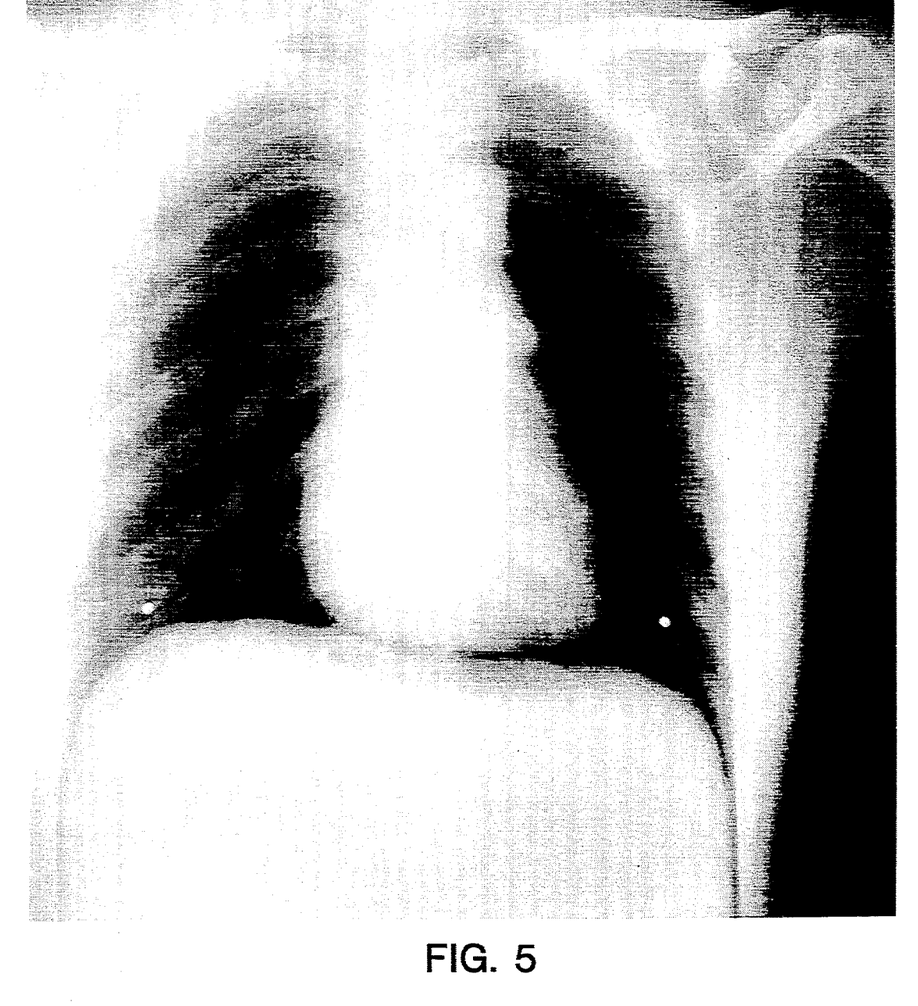
FIG. 5 is a Bayesian restored image of an anthropomorphic chest phantom.

The original measured and the Bayesian restored images of the anthropomorphic phantom are shown in FIGS. 4 and 5 respectively. This Bayesian image was initialized with the measured image and was processed for 30 iterations. Applicants observed improved visualization of the thoracic spine, descending thoracic aorta, and cardiac nodule, as well as the subdiaphragmatic areas of the thorax in the Bayesian image. In addition, the improved contrast and signal-to-noise ratio in the lung results in improved visualization of the pulmonary vasculature of the Bayesian image. The image is equalized by removing the scatter background. While the scatter fraction is higher in the mediastinum than in the lung, the number of scattered photons is higher in the lung due to the much larger total flux in the lung. Thus, with scatter compensation, there is an image equalization since more photons are removed from the lung than from the mediastinum. It is significant that while the contrast has been enhanced by the removal of as much as 90% of the measured photon events in the processed image, the percent noise remained the same rather than increasing by a factor of ten as would be expected from a scatter subtraction.

The 2K images were printed to film and were compared to the unprocessed images by three thoracic radiologists. There was no observed degradation of image resolution.

D. Processing Time

The Bayesian algorithm was implemented on a STARDENT ST 1000 computer with 64 MB of memory. For 1 k images, the algorithm took 3 min/iteration (60 min for 20 iterations). For the 2 k images, the algorithm took 4 times as long. The STARDENT computer had a four processor architecture and the algorithm is easily distributed across multiple processors. Computation speed could be improved with larger memory and more processors.

CONCLUSIONS

The significant contribution of the method of the invention is the improvement of SNR in the Bayesian restored images. The Rose model of vision (see Rose, "The Sensitivity Performance of the Human Eye on an Absolute Scale" *Journal of the Optical Society of America,* 1948, 38:196–208) relates object detectability to the SNR of an object in an image. Thus, the detectability of low contrast objects (such as nodules) may be enhanced by this improvement in SNR.

While window and level operations can modify contrast, noise is boosted in the same operation and SNR is unchanged. Grids and air gaps reduce the number of detected scattered photons at the cost of a (smaller) reduction in primary (non-scattered) photons. For a range of grid designs and air gaps, the net effect is a reduction in the scatter fraction with an increase in SNR. Reported increases in SNR for grids are between 0.5 (lung) and 2.0 (mediastinum). Disadvantages of these techniques include the increased patient dose required to overcome the decrease in primary photons, physical alignment requirements of the grid, and magnification in the air gap images. Neither air gaps nor grids have achieved routine use in portable bedside radiography (although the recently introduced film cassette incorporating a flexible grid with wide acceptance angle may prove practical).

With the availability of digital chest imaging systems, numerical post processing techniques are now an option for reducing the image degradation due to scattered radiation. Several techniques have been suggested for scatter compensation through numerical post processing. Unfortunately, while these previously described techniques improve image contrast, they do not improve image noise and the net results is usually a decrease in SNR.

Applicants have described herein a Bayesian algorithm for use in projection radiography which decreases the effects due to scatter with little increase in noise. The net increase in SNR is superior to that provided using grids and air gaps in the lung, and at least comparable in the mediastinum. In addition, while grids and air gaps provide a limited reduction of scatter (from 0.95 to 0.7 in mediastinum), when combined with the procedure of the invention, further scatter clean up is possible.

Algorithm Utilized in Preferred Embodiment of Method of the Invention

The scatter compensation model is the same as used in the MLEM algorithm described in Floyd et al., "Scatter Compensation for Digital Chest Radiography Using Maximum Likelihood Expectation Maximization" *Investigative Radiology,* 1993, In Press:(May). This model of scatter is analogous to the scatter compensation provided by unified ECT reconstruction. A photon which is initially emitted toward pixel i but scatters so that it is detected at pixel j, is moved back to pixel i. Following earlier work (see Seibert et al , "X-ray Scatter Removal By Deconvolution", *Medical Physics,* 1988, 15:567–575) and (see Floyd et al. "Scatter Compensation in Digital Chest Radiography" *Investigation Radiology,* 1989, 24:30–33), applicants modeled the scatter as a convolution of the non-attenuated distribution with a 2-dimensional radial exponential function. Specifically:

detected flux = K(primary+primary$\alpha$exp($\gamma$|r|)) A1 where  denotes a two dimensional convolution and K is the ratio of the number of direct detected photons to the direct+scattered detected photons.

The exponential function has two free parameters: $\alpha$, the scatter-to-primary ratio; and $\gamma$, a width parameter which is equal to log(4)/FWHM where FWHM is the full-width-at-half-maximum. Values for these two parameters were found from a grid search to minimize the %rms difference between the estimate of the scatter from a deconvolution technique and the measured values of scatter. The parameter search was performed using an image of the anatomical phantom which included 64 scatter values measured simultaneously with the image acquisition using the Posterior Beam Stop (PBS) technique (see Floyd et al., "Posterior Beam Stop Method for Scatter Fraction Measurement in Digital Radiography", *Investigative Radiology,* 1992, 27:119–123). A minimum scatter error was found with a scatter-to-primary ratio $\alpha$ of 2.33 and a RWHM of 3.6 cm.

Bayesian Algorithm

The Maximum Likelihood Expectation Maximization (MLEM) algorithm for scatter reduction in digital chest imaging has been described previously in Floyd et al., "Compensation for Digital Chest Radiography Using Maximum Likelihood Expectation Maximization", *Investigative Radiology,* 1993, In Press:(May). The Bayesian extension of this algorithm is formed by including a priori information about the image. This priori information given by f($\lambda$) is incorporated through Bayes' rule to form the probability distribution of the image vector $\lambda$ conditioned on the data vector y. Specifically:

$$f(\lambda|y) = \frac{f(y|\lambda)f(\lambda)}{f(y)}. \quad\quad A2$$

To form the Maximum a posteriori (MAP) image estimate, applicants estimated the $\lambda$ which maximizes f ($\lambda$/y). If the prior distribution f($\lambda$) is uniform, then Eq. A2 reduces to the ML estimate. Applicants maximized Eq. A2 using the gradient technique of Hebert and Leahy (see Hebert, T. and Leahy, R., "A Generalized EM Algorithm for 3-D Bayesian Reconstruction from Poisson Data Using Gibbs Priors" *IEEE Transactions on Medical Imaging,* 1989, 8:194–202). Since maximizing f is equivalent to maximizing log (f), applicants obtained (ignoring terms which are independent of $\lambda$):

$$\underset{\lambda}{\max} f(\lambda/y) = \underset{\lambda}{\max}[\log f(y|\lambda) + \log f(\lambda)] \quad\quad A3$$

The first term on the right hand side is the maximum likelihood estimation (MLEM) solution. The second term, log f($\lambda$), is where a priori information about the image is included. The prior information regarding image smoothness is imposed by using a Gibbs function. The general form of the Gibbs function used is given by:

$$P(\lambda) = \frac{1}{Z}\exp[-\beta U(\lambda)] \quad\quad A4$$

where $$U(\lambda) = \underset{i,j \in N}{\Sigma} V(\lambda_i - \lambda_j) \quad\quad A5$$

is called the energy function and $\beta$ is an adjustable parameter. Note that with $\beta$=0, the solution reduces to the MLEM solution. As $\beta$ is increased, the solution depends more on the energy function U. While the parameter $\beta$ can be optimized by iteration of grid searches, applicants used the method suggested by Geman and McClure (see Shepp et al. "A Statistical Model for Positron Emission Tomography" *J. Amer Statis Assoc.,* 1985, 80:8–37).

The goal of choosing an energy function is to try and represent some properties which applicants believed represent the underlying medical image. For noise constraint, applicants desired to find an energy function which discriminated noise from anatomical structure. To this end, a potential was selected which depends only on the difference between the pixel and its neighbors. Here, a first order neighborhood of a pixel refers to the four pixels which are adjacent vertically and horizontally in the rectangular image array. A clique is defined as a set of pixels such that each pixel is a neighbor of all other pixels in the clique. For the neighborhood described above (which is defined as a first order neighborhood), cliques consist of either a single pixel, or two vertically or horizontally adjacent pixels. In the sum in Eq. A5, i and j must belong to a clique and the sum is over all cliques. Since the potential only depends on the difference between pixel values, the energy for a pixel at location (x,y) is the sum of the potential function evaluated between (x,y) and the four neighbors: (x,y+1), (x,y−1), (x+1,y), and (x−1,y).

Of the possible potentials, Eq. A6 suggested by Geman and McClure (see Geman et al., "Statistical Methods for Tomographic Image Reconstruction", *Division of Applied Mathematics and Center for Intelligent Control Systems,* Brown University:Technical Report) for ECT will suppress small pixel values differences which were attributed to noise while allowing larger differences which were attributed to structure. Specifically:

$$V(\lambda_j - \lambda_i) = \frac{(\lambda_j - \lambda_i)^2}{\delta^2 + (\lambda_j - \lambda_i)^2} \quad\quad A6$$

The parameter $\delta$ controls the suppression threshold and was held consistent at a value of 0.03.

Thus, applicants have developed a novel projection radiography image enhancing technique utilizing a restoration algorithm which simultaneously (1) removes the effect of any blurring image degradation such as the effects of scattered radiation and (2) decreases the noise in the resulting image. The removal of scattered radiation and decrease of noise are controlled by three adjustable parameters in the algorithm, and values for these parameters can be adjusted to trade-off scatter compensation for noise reduction. While scatter compensation and noise reduction are significantly improved over conventional techniques such as spacial frequency filters, the algorithm can be optimized to provide more of one than the other.

It will be understood that various details of the invention may be changed without departing from the scope of the invention. Furthermore, the foregoing description is for the purpose of illustration only, and not for the purpose of limitation-the invention being defined by the claims.

What is claimed is:

1. A method for increasing the signal-to noise ratio (SNR) in projection radiography imaging comprising:
   (a) subjecting an object under examination to projection radiography to measure the transmission of photons through the object so as to obtain measured digital imaging data;
   (b) altering said measured digital imaging data to compensate for blurring degradation from said projection radiography;
   (c) altering said measured digital imaging data to compensate for noise therein from said projection radiography;
   (d) forming an enhanced image of the object under examination from said measured digital imaging data to have an increased signal-to-noise ratio (SNR); and
   (e) analyzing the enhanced image for interpretation thereof.

2. The method of claim 1 wherein steps (c) and (d) are repeated to obtain said enhanced image.

3. The method of claim 1 wherein said blurring degradation consists of scattered radiation.

4. The method of claim 1 wherein said digital imaging data is altered to compensate for blurring degradation by using a predetermined maximum likelihood expectation maximization (MLEM) algorithm.

5. The method of claim 4 where said altered digital imaging signal is altered to compensate for noise therein by using predetermined Gibbs prior distribution data.

6. The method of claim 1 wherein said digital imaging data is altered to compensate for blurring degradation and to compensate for noise therein by a predetermined Bayesian estimation algorithm.

7. The method of claim 6 wherein said Bayesian estimation algorithm comprises a Bayesian Maximum a posteriori (MAP) estimation algorithm.

8. A method for increasing the signal-to noise ratio (SNR) in projection radiography imaging comprising:
   (a) subjecting an object under examination to projection radiography to measure the transmission of photons through the object so as to obtain measured digital imaging data;
   (b) altering said measured digital imaging data by using a predetermined maximum likelihood expectation maximization (MLEM) algorithm to compensate for scattered radiation from said projection radiography;
   (c) altering said measured digital imaging data to compensate for noise therein from said projection radiography by using predetermined Gibbs distribution data;
   (d) forming an enhanced image of the object under examination from said measured digital imaging data to have an increased signal-to-noise ratio (SNR); and
   (e) analyzing the enhanced image for interpretation thereof.

9. The method of claim 8 wherein steps (c) and (d) are repeated to obtain said enhanced image.

10. The method of claim 8 wherein said digital imaging data is altered to compensate for scattered radiation and to compensate for noise therein by a predetermined Bayesian estimation algorithm.

11. The method of claim 10 wherein said Bayesian estimation algorithm comprises a Bayesian Maximum a posteriori (MAP) estimation algorithm.

* * * * *